US00PP16175P3

(12) United States Plant Patent

Little et al.

(10) Patent No.: US PP16,175 P3
(45) Date of Patent: Dec. 27, 2005

(54) PEACH TREE NAMED 'JANET'

(50) Latin Name: *Prunus persica*
Varietal Denomination: Janet

(76) Inventors: Gary W. Little, 1215 Block Rd., Gridley, CA (US) 95948; Janet D. Little, 1215 Block Rd., Gridley, CA (US) 95948

( * ) Notice: Subject to any disclaimer, the term of this patent is extended or adjusted under 35 U.S.C. 154(b) by 0 days.

(21) Appl. No.: 10/828,689

(22) Filed: Apr. 21, 2004

(65) Prior Publication Data

US 2005/0241038 P1 Oct. 27, 2005

(51) Int. Cl.[7] ..... A01H 5/00

(52) U.S. Cl. ..... Plt./197

(58) Field of Search ..... Plt./197

*Primary Examiner*—Anne Marie Grunberg
*Assistant Examiner*—June Hwu
(74) *Attorney, Agent, or Firm*—Richard A. Ryan

(57) ABSTRACT

A new and distinct variety of peach tree which is somewhat similar to Bowen peach tree (unpatented) from which it is a chance seedling but from which it is distinguished by producing an early ripening fruit which are mature 22 to 24 days before Bowen and seven days before 'Loadel' with good exterior color and uniform flesh color which is mature for commercial harvesting and shipment approximately July 8 to 10 in a normal year.

1 Drawing Sheet

CROSS-REFERENCE TO RELATED APPLICATIONS

None.

Variety denomination: Variety of *Prunus persica,* denominated as 'Janet'.

BACKGROUND OF THE INVENTION

1. Field of the Invention

The present invention refers to a new and distinct variety of peach tree which will hereinafter be denominated as the 'Janet' peach tree which produces clingstone fruit which are mature for commercial harvesting and shipment approximately July 8 to 10 in a normal growing year in the Sacramento Valley of Northern California as an early peach clingstone fruit for processing with a red blush coloration which matures approximately seven days before the 'Loadel' (un-patented) clingstone peach.

2. Background

In the development of new commercial varieties of fruit, specific characteristics places a premium on early or late maturing, in the growing. However, many other varieties have small size, lack of flavor, or coloration. In some instances there are other undesirable characteristics that decrease the commercial success, such as lack of color, size, good flavor and good color. At the same time it must have a different maturity date than that of similar fruit. This new invention meets all of the aforementioned criteria and therefore is of commercial appeal to the processor.

BRIEF SUMMARY OF THE INVENTION

The 'Janet' is characterized by producing large clingstone fruit with good yellow color and red blush coloration and is ripe for commercial harvesting and shipment July 8 to 10 in the Sacramento Valley of Northern California. The new variety is most similar to the 'Loadel' peach tree (un-patented) and the Bowen peach tree (un-patented) from which it is a chance seedling, and from which it is distinguishable in that it ripens approximately 7 days before 'Loadel' and 22 to 24 days before 'Bowen' peach trees and that the fruit is slightly larger in size than the aforementioned varieties. The fruit of this new variety possesses good firmness, color as well as flavor which is greatly acceptable for an early ripening clingstone peach.

ORIGIN AND ASEXUAL REPRODUCTION OF THE NEW VARIETY

The present variety of peach tree was discovered by the inventors in their peach orchard located at the southwest intersection of Pennington Road and Billings Road, 2 miles outside of Live Oak, Calif. in Sutter County. The inventors discovered this seedling in a commercial planting at 'Bowen' (unpatented) clingstone peach trees in the early 1990s. The new variety was first asexually reproduced by the inventors in 1993 by budgrafting on 'Lovell' peach rootstock (unpatented) at a location approximately two miles southwest of Gridley, Calif. on Block Road. The asexually reproduced trees first bore fruit of the new variety in July 1995. The inventor carefully compared the asexually reproduced tree with the mother seedling including the fruit thereof and is in all respect identical, stable and reproduces to type in successive generations of asexual reproduction.

BRIEF DESCRIPTION OF THE DRAWING

The accompanying drawing is a color photograph showing fruit and foliage of the new variety. The fruit on the bottom right displays a fruit cut in half with the pit in place while the half on the left shows the pitwell. The next row upward shows the suture as wells as the stem end on the stem end on the left displays a side view with the cheek surface. The fruit on the next row upward displays the apical end of the fruit. The top of the photograph shows the foliage typical of this new variety.

DETAILED DESCRIPTION

Referring more specifically to the pomological description of this new and distinct variety of peach tree, the following has been observed for a tree approximately ten years old, under the ecological conditions prevailing in the orchard, located near Gridley, Calif. in the Sacramento Valley of Northern California. All major color designations are by reference to the Dictionary of Color by Maerz & Paul, First Edition, 1930. Common color names are occasionally employed.

Tree:

*Size.*—Large — Approximately 15 feet high and 15 feet in width.

*Vigor.*—Vigorous.

*Figure (form).*—Upright and spreading with open vase system of training.

*Production.*—Very good — 24 ton/acre.

*Regularity of bearing.*—Regular every year.

Trunk:

*Size.*—At 18 inches above the ground, circumference is 22 inches.

*Surface texture.*—Moderately rough.

*Color.*—PI. 15 A8 (Winter Leaf, Cashew Nut, Beach Tan Sedge).

*Lenticels.*—Approximately 22 small lenticels per square inch — oval shape — 6.35 mm to 7.94 mm (0.25 inch to 0.3125 inch). Color Code — PI.7 E10 (Chestnut Brown).

*Bark color.*—PI.6 A9 (Maren).

Branches:

*Size.*—14 inches in circumference at 42 inches above ground.

*General.—Four scaffold branches with* 54° angle.

*Surface texture.*—Slightly rough.

*Color.*—Mature branches — PI.7 E10 (Chestnut Brown).

*Color.*—Immature branches — PI.17 L7 (Viridine y).

Leaves:

*Size.*—Medium to large.

*Length.*—150 to 155 mm (5.51 to 6.50 inches).

*Width.*—33 to 38 mm (1.30–1.50 inches).

*Thickness.*—Normal for peach.

*Shape.*—Base Shape — Lanceolate, leaf tip acuminate, texture smooth.

*Color.*—Upwardly disposed surface — PI.23 L6 (Cypress Green and Forest Green), Downwardly disposed surface — PI.22 H7 (Garland Green).

*Marginal form.*—Crenate.

*Leaf vein.*—Color PI.20 K5 (Verdant Green). Thickness — 1 mm (0.04 inch).

*Glandular characteristics.*—Reniform alternate at base of leaf. Color code — PI. 24 L7 (Near Mt. Vernon Green).

*Number of glands.*—Usually 2 to 3 on each side of petiole of leaf base.

*Petiole.*—Size — Medium. Length — 8 to 11 mm (0.31–0.43 inch). Diameter — 1 to ½ mm (0.059 inch). Color Code — PI.20 A7 (Fairy Green).

*Stipules.*—Very small, 1 mm or less — reddish brown — PI.7 E6 Canyon.

Flowers:

*Flower buds.*—Hardy under Sacramento Valley climatic conditions. Size — Length — 7 to 11 mm (0.28 to 0.43 inch). Width — 25 mm (0.98 inch). Shape — Generally conic. Color code — PI.3 F3 (Bridal Rose, Light Pink) and pubescent. Calyx — 5 sepals — Color — PI.6 L8 (Dark Cardinal Rose) toward the base and PI.7 L7 (Maroon).

*Generally.*—Showy, abundant.

*Color.*—PI.3 F3 (Bridal Rose).

*Date of bloom.*—35 to 40% by March 11 and 100% by March 18.

*Size.*—Average diameter 2.5 mm (0.98 inch).

*Petals.*—Five in number. Length 10 mm (0.39 inch), width 9 to 10 mm (0.35 to 0.39 inch) with slightly notched margins.

*Form.*—Broadly ovate.

*Margins.*—Moderately undulated with somewhat rounded edges.

*Color.*—Margins PI. 3 I3 (Weigel).

*Petal claws.*—Broadly truncate — width 1 to 2 mm (0.037 to 0.038 inch).

*Flower pedicel.*—Very short, 2 mm (0.079 inch), Color PI.19 K6 (Seagreen). Anthers — small — Color PI.7 J5 (Tapestry Red). Stamens — Approximately 40, Length 10 to 13 mm (0.39 to 0.51 inch). Color when first open — PI.4 J3 (Azalea), then change to PI.2 A1 (White).

*Filament.*—Color PI.5 J7 (Harvard Crimson Jockey).

*Pistil.*—Length 12 mm (0.47 inch). Number — 1. Color PI.17 C2 (Seaform y). Surface — Slightly pubescent.

*Pollen.*—Color — 9 K 6 (Yellow).

Fruit:

*Date of maturity.*—July 8 to 9.

*Size.*—Diameter Axial Plane — 80 mm (3.15 inches). Transverse in Suture Plane — 70 to 75 mm (2.26 to 2.95 inches). Transverse in Right Angles to suture Plane — 75 mm (2.85 inches).

*Weight.*—Average — 5.9 oz.

*Form.*—Nearly uniform. Symmetrical — slightly asymmetrical.

*Suture.*—Shallow.

*Ventral surface.*—Slightly uneven.

*Stem cavity.*—Length — 28 to 35 mm (1.1 to 1.38 inches). Width — Average 15 mm (0.59 inch). Depth — 16 mm (0.63 inch).

*Shape.*—Ovate.

*Base shape.*—Medium wide and rounded.

*Stem.*—Short — 8 mm (0.31 inch) to 4 mm (0.16 inch).

*Apex.*—Pointed and prominent.

*Skin.*—Thickness normal for clingstone peach-fruit.

*Skin texture.*—Firm — Smooth.

*Tendency to split.*—None observed.

*Color code.*—Blush — PI.6 L6 (Chianti Antique Ruby), PI.9 K6 (Forsythia). Flesh Color — PI.9 L8 (Cadmium y).

*Surface of pit cavity.*—PI.12 L9 (Yucatan Cathay-Mexican+French y).

*Color of pit cavity wall.*—PI.12 L9 (Yucatan Cathay-Mexican+French y).

*Juice production.*—Moderate.

*Flesh fibers.*—None.

*Flesh aroma.*—Slight, pleasant.

*Flavor.*—Very good.

*Texture.*—Firm.

*Ripening.*—Even.

*Processing quality.*—Very good.

Stone:

*Attachment.*—Clingstone.

*Fibers.*—Few and thick.

*Size.*—Length 35 mm (1.38 inch), width 25 mm (0.98 inch) and thickness 20 mm (0.79 inch).

*Form.*—Oval.

*Apex.*—Slightly rounded.

*Color code.*—(When dry) PI.12 L 12 (Punjab).

*Base.*—Rounded with flattened center.

*Sides.*—Slightly unequal.

*Ridges.*—On both sides with narrow ridge on ventral side.

*Tendency to split.*—None observed.

Use: Canning — For processing as canned peaches.

Shipping quality: Good — due to firm nature of fruit, it will ship and handle very well at time of harvesting and refrigeration of fruit.

Plant/fruit disease and pest resistance/susceptibility: None observed.

Keeping quality: Good shelf life. Kept at room temperature for 3 to 5 days. Has kept in cold storage for up to 2 weeks.

Like most peach trees in California, the new variety has winter hardiness and is not susceptible to damage during the dormant. There is no evidence of any particular susceptibly of the tree or fruit to heat.

Although the new variety of peach tree possesses the described characteristics noted above based on the growing conditions prevailing near Gridley, Calif. in the Sacramento Valley of Northern California, it is to be understood that variations in the usual magnitude and characteristics incident to changes in growing conditions, irrigation, fertilization, pruning, pest control, climatic variation and the like are to be expected. It should also be realized by those skilled in the art that such equivalent constructions do not depart from the spirit and scope of the invention as set forth in the appended claim.

Having thus described and illustrated the new variety of peach tree, what is claimed is:

1. A new and distinct variety of peach tree substantially as illustrated and described herein.

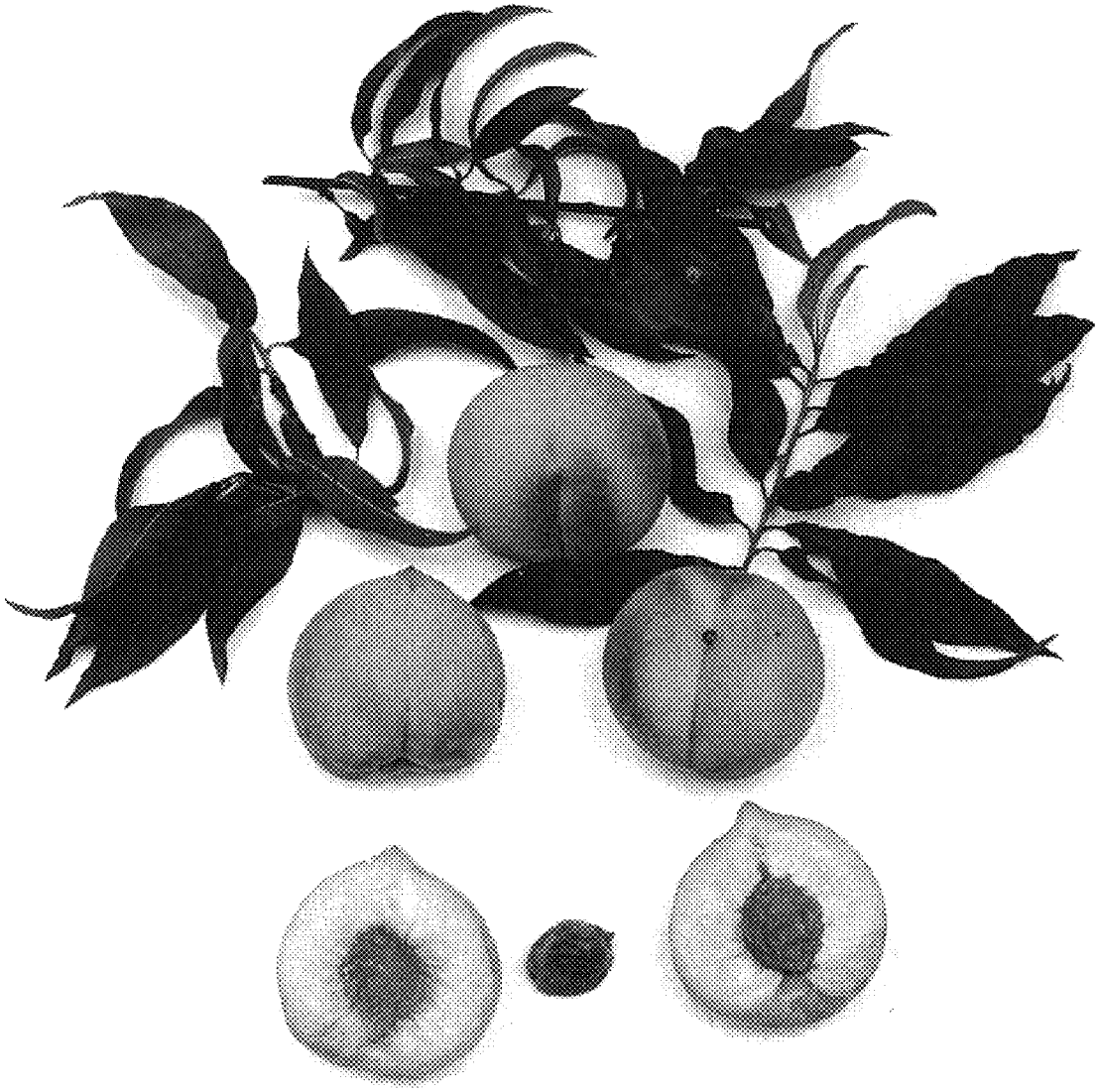

* * * * *